United States Patent

Risung et al.

Patent Number: 5,723,015
Date of Patent: Mar. 3, 1998

[54] ELBOW PROSTHESIS

[76] Inventors: Finn Risung, Borgekroken 31, N-3711 Skien; Knut Johnsen, Gamleveien 13, N-1406 Hebekk, both of Norway

[21] Appl. No.: 501,115
[22] PCT Filed: Feb. 9, 1994
[86] PCT No.: PCT/NO94/00033
§ 371 Date: Sep. 26, 1995
§ 102(e) Date: Sep. 26, 1995
[87] PCT Pub. No.: WO94/17758
PCT Pub. Date: Aug. 18, 1994

[30] Foreign Application Priority Data

Feb. 10, 1993 [NO] Norway .................. 930460

[51] Int. Cl.$^6$ .................. A61F 2/38
[52] U.S. Cl. .................. 623/20
[58] Field of Search .................. 623/20, 21, 18

[56] References Cited

U.S. PATENT DOCUMENTS

| | | | |
|---|---|---|---|
| 3,760,427 | 9/1973 | Schultz | 623/20 |
| 3,795,922 | 3/1974 | Herbert | 623/20 |
| 3,816,854 | 6/1974 | Schlein | . |
| 3,934,272 | 1/1976 | Wearne | 623/20 |
| 4,059,854 | 11/1977 | Laure | 623/21 |
| 4,383,337 | 5/1983 | Volz | 623/20 |
| 4,538,306 | 9/1985 | Dörre | 623/20 |
| 4,923,472 | 5/1990 | Ugolini | 623/20 |
| 5,314,484 | 5/1994 | Huene | 623/20 |
| 5,370,701 | 12/1994 | Finn | 623/20 |

FOREIGN PATENT DOCUMENTS

| | | |
|---|---|---|
| A 331384 | 8/1976 | Austria . |
| 2351912 C2 | 7/1983 | Germany . |

*Primary Examiner*—Michael J. Milano
*Attorney, Agent, or Firm*—Merchant, Gould, Smith, Edell, Welter & Schmidt, P.A.

[57] ABSTRACT

An implantable elbow prosthesis (1) comprises an ulnar component (2) and a humeral component (3) wherein the head (21) of the ulnar component is designed in a bifurcated shape with two horns (22, 23) and the head (31) of the humeral component comprises a rotatable spindle (34) between two projecting flanges (32, 33). The joint component of the prosthesis is formed by arranging the head (21) of the ulnar component to engage with the spindle (34) of the humeral component. In each of the horns (22, 23) on the ulnar component (2) there is provided a groove (24, 25) which terminates in a respective blind hold (24, 25) on each horn (22, 23). A C-ring form of clip (4) connects the heads (21, 31) of the ulnar component and the humeral component, while maintaining the desired degree of freedom of movement for the elbow joint and a predetermined tolerance of movement. The clip (4) embraces the spindle (34) on the humeral component (3) with a clearance (5) between the arc (43) of the clip and the spindle and is locked to the ulnar component (2), the ends (41, 42) of the clip being inserted into the grooves (24, 25) on the horns (22, 23) of the ulnar component and engaging with the blind holes (26, 27). This ensures that the ulnar component (2) does not lose its grip on the spindle (34) of the humeral component, while at the same time the desired play is obtained in the actual joint connection, a vital circumstance for the functional characteristics of the prosthesis.

6 Claims, 2 Drawing Sheets

1

ELBOW PROSTHESIS

BACKGROUND OF THE INVENTION

1. Field of the Invention

The invention concerns an elbow prosthesis for implantation in destroyed elbow joints, with an ulnar component and a humeral component in tissue-compatible material, wherein the head of the ulnar component is designed in a bifurcated form with two horns, wherein the head of the humeral component comprises a rotatable, replaceable spool or spindle of a tissue-compatible and strong plastic material between two projecting flanges and wherein the joint component of the prosthesis is formed by the head of the ulnar component being arranged to engage with the rotatable spindle of the humeral component.

2. Description of Related Art

A large number of elbow prostheses are known in the literature and the art EP-0098 466 shows an elbow prosthesis wherein a fixed spindle on the humeral component engages with a substantially cylindrical sliding piece in a cut-out on the spindle and wherein the sliding piece is anchored on a shaft which is attached to the ulnar component. The sliding piece is thereby rotatably mounted in the fixed spindle and is locked to it by means of a sleeve which has a C-shaped cross section and which is pushed over the spindle.

Furthermore EP-A-0 057 793 shows an elbow prosthesis of a similar kind with a spindle-like element on the humeral component and a bifurcated element on the ulnar component. The object is to achieve an optimum joining of the joint components and ensure stability, low loading and mobility with a minimum removal of bone tissue.

SUMMARY OF THE INVENTION

The basis for the present application is NO patent application no. 76 3136 which was submitted on 14. Sep. 1976 by one of the present inventors and shelved on 4. Nov. 1977 without having been made generally available. In this an elbow prosthesis is shown with a rotatable spindle or spool which engages with a bifurcated section of the second prosthesis component and wherein the prosthesis components are attached in the usual way to the medullary cavities in those bones which are to be connected, i.e. the humerus and the ulna. This prosthesis has later become known in practice and it will be referred to here in its entirety as an example of the state of the art which forms the basis of the present invention.

The known prosthesis consists of several sizes of humeral components and several sizes of ulnar components with a common joint component, thus enabling for each patient the selection of the component size which is best suited to the individual bones. The joint connection is free and this prosthesis is therefore dependent on good ligaments and muscle tendons in order to keep the joint in place. If the ligaments are not adequate, e.g. due to fracture and injury, the prosthesis will be able to come out of joint.

Thus the object of the present application is to modify the known prosthesis in such a way that the free joint connection can be blocked and convened to a so-called "semi-constrained" prosthesis which can also be used where the ligaments are not adequate and there is a risk of the prosthesis coming out of joint.

This object is achieved with an elbow prosthesis according to the present invention, characterized in that in each of the horns on the ulnar component there is provided a groove which terminates in a respective blind hole on each horn, the blind holes being approximately diametrically opposite each other in relation to the ulnar component's joint centre, that the elbow prosthesis contains a C-ring-like clip ganged to connect the heads of the ulnar component and the humeral component while maintaining the desired degree of freedom of movement for the elbow joint and a predetermined tolerance of movement, and that the clip embraces the spindle on the humeral component with a clearance between the arc of the clip and the spindle and is locked to the ulnar component, the ends of the clip being inserted into the grooves on the horn of the ulnar component and engaging with the blind holes. Further features and advantages of the elbow prosthesis according to the invention are described in the attached independent claims.

BRIEF DESCRIPTION OF THE DRAWINGS

The elbow prosthesis according to the invention will now be described in more detail in connection with an embodiment and with reference to the attached drawing.

DESCRIPTION OF THE ILLUSTRATED EMBODIMENTS

Figure 1A:
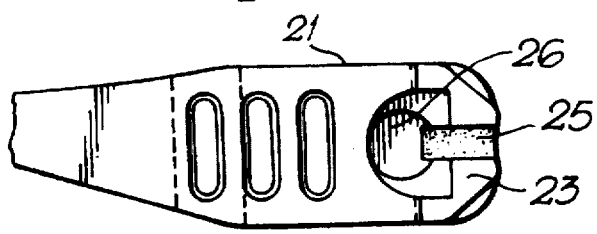
FIGS. 1a–1c show schematically the head of the ulnar component of the prosthesis seen from the rear, from the side and from above towards the opening between the horns respectively.
Figure 1B:
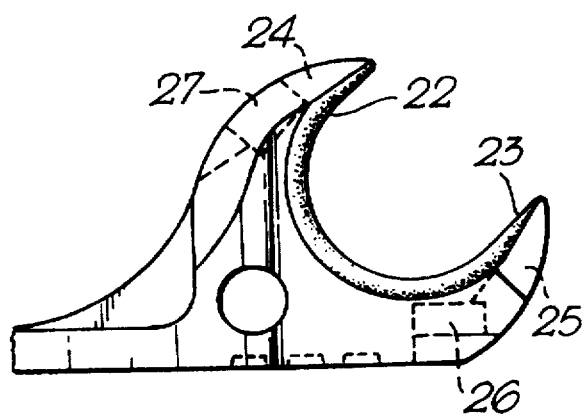
Figure 1C:
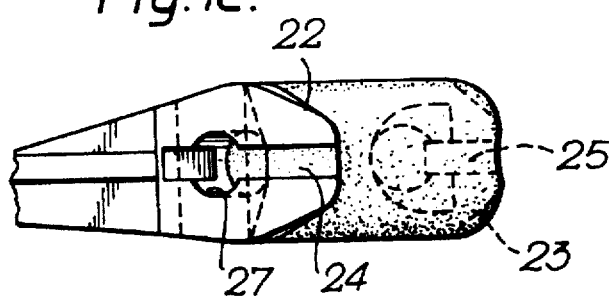

With reference to FIG. 1b it can be seen that the head 21 of the ulnar component 2 forms a bifurcated structure with two horns 22,23, the ends of which project somewhat beyond a diameter in the fork arc. On the outside of each horn 22,23 there are formed grooves 24,25 which each terminate in a bore or blind hole 26,27 in each horn. Moreover in FIG. 3a and 3b it is shown how the ends 41,42 of a C-ring-like clip 4 can engage with the head 21 of the ulnar component, the ends 41,42 of the clip being inserted into and in abutment with the grooves 24,25 on the horn 22,23 of the ulnar component and engaging with the blind holes 26,27 in the horns.

Figure 2A:
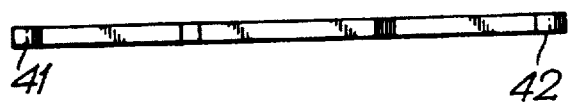
FIGS. 2a–2c show the clip of the present invention seen in a planar state from the side and in a top view respectively and from the side after the clip has been bent into a C-ring shape.
Figure 2B:
Figure 2C:
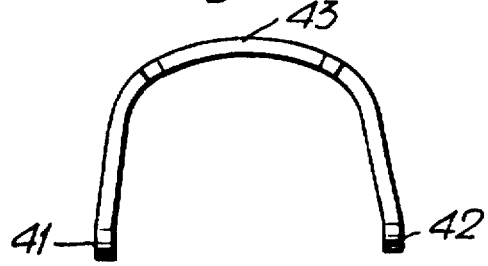
Figure 3A:
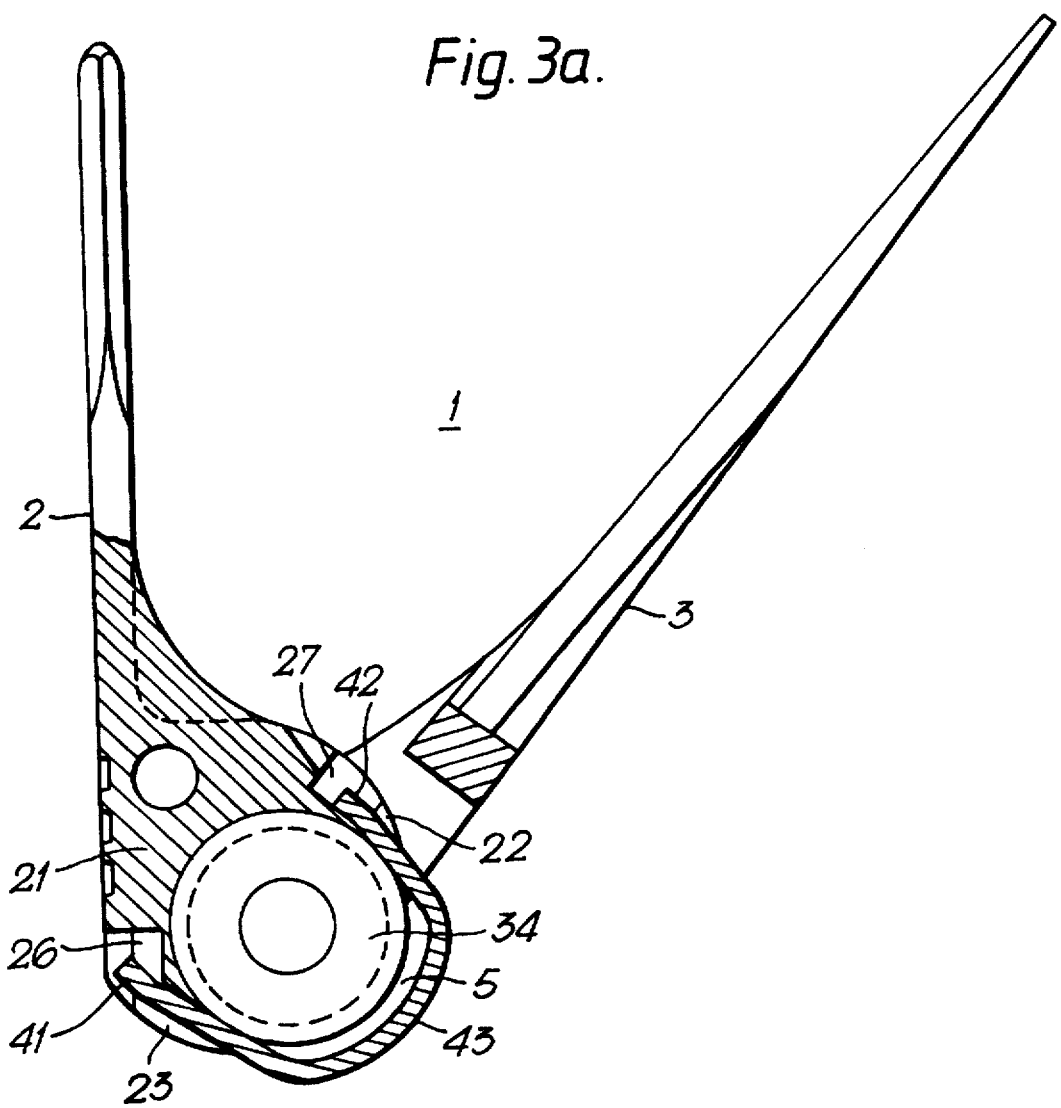
FIGS. 3a and 3b illustrate the elbow prosthesis according to the invention in an assembled condition, seen from the side and from the rear along the axis of the ulnar component respectively and with the clip inserted.
Figure 3B:
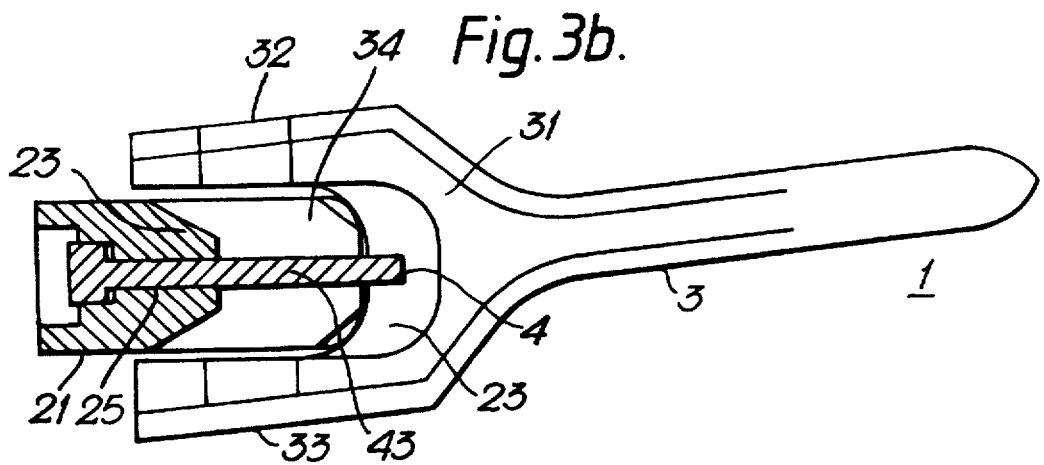

This C-ring-like clip 4 is illustrated in more detail in FIG. 2a–2c. In the example shown the clip 4 is in the form of an approximately 40 mm long sheet component of, e.g. a titanium alloy and normally has a cross section of approximately 1.5 by 3 min. The ends 41,42 of the clip are extended to form a semicircular sheet component with a diameter of approximately 5 mm. The clip 4 is bent into a C-ring shape as illustrated in FIG. 2c, the arc 43 in the C-ring being substantially composed of a slightly wider section of the clip, while between this section and the ends 41,42, the clip is made somewhat narrower in order to provide optimum strength and elasticity. The inside of the arc 43 on the clip 4 can be polished on those surfaces which can enter into contact with the spindle 34 on the humeral component 3 in order to prevent unnecessary wear. When locking the prosthesis the ends 41,42 of the clip 4 are inserted into the grooves 24,25 in the horns 22,23 on the ulnar component 2, as shown in FIGS. 3a and 3b, these grooves being provided approximately diametrically opposite each other in relation to the joint centre of the ulnar component. The clip 4 is passed over the spindle 34 which is mounted on the humeral component 3 and locks it to the ulnar component 2, the ends 41,42 of the clip engaging in the blind holes 26,27 on the ulnar component. The groove 24,25 in each of the horns 22,23 has a width corresponding to that of the clip, thus ensuring that after being attached the clip 4 will remain securely in place without the occurrence of any lateral movements which may cause wear. The arc 43 in the clip 4 is made wide enough to permit sufficient mobility between the humeral component 3 with the spindle 34 and the ulnar component 2 and a suitable elasticity to ensure that the clip 4 is securely attached when its end 41,42 have engaged with the blind holes 26,27 on the horn 22,23 of the ulnar component. A humeral component 3 has a head 31 that includes a rotatable spindle 34 between two projecting flanges 32 and 33. The ulnar component 2 is thereby securely attached to the humeral component 3 and holds the spindle 34 of the humeral component in a secure grip, while at the same time some play is permitted in the actual joint connection, a vital circumstance for the functional characteristics of the prosthesis. The mounted prosthesis with the clip in place is illustrated in FIGS. 3a and 3b and FIG. 3a clearly shows the clearance 5 between the spindle 34 and the arc 43 of the clip and also that the ends of the horns 22,23 on the ulnar component 2 project somewhat above a diameter on the spindle 34, e.g. approximately 5 mm beyond this diameter. This means that the clip 4 cannot work loose or fall off unless it breaks. Any tension load on the clip 4 will in fact act outwards through the middle of the arc 43 of the clip and the tension load will therefore only help to further tighten the clip. The ends of the clip will never be able to be pushed out of the bores by the forces acting on the prosthesis during use.

The clip and the other metal components in the prosthesis are made of tissue-compatible material, preferably titanium alloy, as are the other metal components in the prosthesis, thus making the prosthesis very strong and durable, e.g. it has a tensile strength of several thousand kilonewton.

The ulna component 2 and the clip 4 are designed in such a manner that the clip can be fitted at any time in the course of an operation, even after the actual prosthesis has been cemented into the bones and the joint put in place. Similarly, the clip can also be easily removed if it subsequently proves to be unnecessary, possibly by means of a subsequent operation.

Thus by means of the present invention an elbow prosthesis has been provided which can also be used where the ligaments are not adequate, thereby eliminating any risk of the prosthesis coming out of joint.

We claim:

1. An elbow prosthesis for implantation in destroyed elbow joints, with an ulnar component and a humeral component of a tissue-compatible material, wherein the head of the ulnar component is designed in a bifurcated form with two horns, wherein the head of the humeral component comprises a rotatable, replaceable spindle of a tissue-compatible and strong plastic material between two projecting flanges, and wherein the joint component of the prosthesis is formed by the head of the ulnar component being arranged to engage with the rotatable spindle of the humeral component, characterized in that in each of the horns on the ulnar component there is provided a groove which terminates in a respective blind hole on each horn, the blind holes being approximately diametrically opposite each other in relation to the joint centre of the ulnar component, that the elbow prosthesis includes a C-ring-like clip arranged to connect the heads of the ulnar component and the humeral component while maintaining a desired degree of freedom of movement for the elbow joint and a predetermined tolerance of movement, and that the clip embraces the spindle on the humeral component with a clearance between an arc of the clip and the spindle and is locked to the ulnar component by ends of the clip being inserted in the grooves on the horns of the ulnar component and engaging with the blind holes.

2. An elbow prosthesis according to claim 1, characterized in that the clip is made of a tissue-compatible material, preferably titanium alloy.

3. An elbow prosthesis according to claim 2, characterized in that the ends of the clip are formed as a sheet-shaped extension with an approximately semicircular shape and with a maximum width of about 5 mm.

4. An elbow prosthesis according to claim 3, characterized in that the grooves in the horn of the ulnar component have a width corresponding to a width of the clip between the arc of the clip and its ends.

5. An elbow prosthesis according to claim 4, characterized in that the ends of the horns on the head of the ulnar component each project beyond a diameter of the spindle on the humeral component when the prosthesis is mounted, preferably by approximately 5 mm.

6. An elbow prosthesis according to claim 5, characterized in that the clip is arranged to be installed or removed during or after the installation of the prosthesis.

* * * * *